(12) United States Patent
Newlin et al.

(10) Patent No.: US 8,959,617 B2
(45) Date of Patent: *Feb. 17, 2015

(54) AUTHORIZATION SCHEME TO MINIMIZE THE USE OF UNAUTHORIZED MEDICAL DEVICE DISPOSABLES ON A MEDICAL DEVICE INSTRUMENT

(71) Applicant: Fenwal, Inc., Lake Zurich, IL (US)

(72) Inventors: Douglas Newlin, Wheaton, IL (US); Kevin Krause, Bartlett, IL (US); Robert Crampton, Gurnee, IL (US); John T. Foley, Wheeling, IL (US); Brian Case, Lake Villa, IL (US); William Cork, Lake Bluff, IL (US)

(73) Assignee: Fenwal, Inc, Lake Zurich, IL (US)

( * ) Notice: Subject to any disclaimer, the term of this patent is extended or adjusted under 35 U.S.C. 154(b) by 155 days.

This patent is subject to a terminal disclaimer.

(21) Appl. No.: 13/833,883

(22) Filed: Mar. 15, 2013

(65) Prior Publication Data

US 2013/0222108 A1 Aug. 29, 2013

Related U.S. Application Data

(63) Continuation of application No. 12/708,964, filed on Feb. 19, 2010, now Pat. No. 8,539,573.

(51) Int. Cl.
*G06F 7/04* (2006.01)
*G06F 21/00* (2013.01)
(Continued)

(52) U.S. Cl.
CPC . *G05B 1/00* (2013.01); *G06F 21/31* (2013.01); *G06F 2221/2141* (2013.01);
(Continued)

(58) Field of Classification Search
CPC ............ G06F 21/31; G06F 2221/2141; G06F 19/3418; G06F 19/3406; H04L 63/08; H04L 63/083
USPC ............. 726/17; 713/182; 600/300; 604/6.01
See application file for complete search history.

(56) References Cited

U.S. PATENT DOCUMENTS

| | | | |
|---|---|---|---|
| 7,965,845 B2 | 6/2011 | Baldrus et al. | |
| 2002/0038392 A1 | 3/2002 | De La Huerga | |

(Continued)

FOREIGN PATENT DOCUMENTS

| | | | |
|---|---|---|---|
| CN | 1977513 A | 6/2007 | |
| CN | 101394279 A | 3/2009 | |

(Continued)

OTHER PUBLICATIONS

International Bureau "Search Report," issued in connection with International Application No. PCT/IB2011/050827, mailed on Sep. 27, 2011, 4 pages.

(Continued)

*Primary Examiner* — Aravind Moorthy
(74) *Attorney, Agent, or Firm* — Becker Patent Law, LLC

(57) ABSTRACT

Systems, methods, apparatus, and computer readable media are provided for disposable component authentication with respect to a biological fluid processing device instrument. An example instrument authentication system includes a computer facilitating configuration and operation of the biological fluid processing instrument using a disposable component. A first interface is provided by the computer and is used by a service technician to configure the biological fluid processing instrument for a number of disposable components and to provide a service technician with a validation code. A key generator is to accept the validation code from the service technician and generate an authentication key in response to the entered validation code. A second interface is provided by the computer, the second interface prompting the service technician to enter an authentication key, wherein the authentication key authorizes use of a certain number of disposable components for the biological fluid processing instrument.

5 Claims, 10 Drawing Sheets

(51) Int. Cl.
*A61B 5/00* (2006.01)
*A61M 37/00* (2006.01)
*G05B 1/00* (2006.01)
*A61M 1/36* (2006.01)
*H04L 9/32* (2006.01)
*G06F 21/31* (2013.01)
*H04L 29/06* (2006.01)
*G06F 19/00* (2011.01)

(52) U.S. Cl.
CPC .......... *H04L 63/083* (2013.01); *G06F 19/3406* (2013.01); *H04L 63/08* (2013.01); *G06F 19/3418* (2013.01); *A61M 1/3693* (2013.01); *A61M 2205/12* (2013.01); *A61M 2205/502* (2013.01); *A61M 2205/60* (2013.01); *H04L 9/3226* (2013.01); *H04L 2209/80* (2013.01); *H04L 2209/88* (2013.01)
USPC ............. 726/17; 713/182; 600/300; 604/6.01

(56) References Cited

U.S. PATENT DOCUMENTS

| | | |
|---|---|---|
| 2003/0130567 A1 | 7/2003 | Mault et al. |
| 2008/0176232 A1* | 7/2008 | Lee et al. ........................ 435/6 |
| 2008/0287889 A1 | 11/2008 | Sharvit et al. |
| 2009/0204075 A1 | 8/2009 | Simpson |
| 2010/0115279 A1 | 5/2010 | Frikart et al. |
| 2011/0006878 A1 | 1/2011 | Nyffeler et al. |

FOREIGN PATENT DOCUMENTS

| | | |
|---|---|---|
| CN | 101981561 A | 2/2011 |
| WO | 2009120231 A | 10/2009 |
| WO | 2011101836 A | 8/2011 |

OTHER PUBLICATIONS

International Bureau "Written Opinion," issued in connection with International Application No. PCT/IB2011/050827, mailed on Sep. 27, 2011, 4 pages.

International Searching Authority, "International Preliminary Report on Patentability," issued in connection with International Application Serial No. PCT/IB2011/050827, mailed on Aug. 30, 2012, 6 pages.

Search Report for CN Application No. 201180003402.1 dated May 20, 2014, 2 pages.

* cited by examiner

US 8,959,617 B2

AUTHORIZATION SCHEME TO MINIMIZE THE USE OF UNAUTHORIZED MEDICAL DEVICE DISPOSABLES ON A MEDICAL DEVICE INSTRUMENT

CROSS-REFERENCE TO RELATED APPLICATIONS

This is a continuation application of U.S. patent application Ser. No. 12/708,964, filed Feb. 19, 2010, which is incorporated by reference herein.

FIELD OF THE INVENTION

The present invention relates generally to methods, systems, and apparatus to authorize a medical device instrument, and more particularly, to methods, systems, and apparatus to authenticate usage of a disposable component in a medical device instrument using an authorization code.

BACKGROUND OF THE INVENTION

One example of a medical device instrument is an apheresis instrument. An apheresis instrument is used to separate blood components from whole blood. Such apheresis instruments are commercially available from various sources, including the Amicus® instrument and the ALYX™ blood processing system which are available from Fenwal Inc. of Lake Zurich, Ill. Such instruments, also known as "separators", typically separate a selected blood component from whole blood by passing the blood of a donor through the instrument to separate one or more blood components from the whole blood. The remainder of the whole blood is then returned to the circulatory system of the donor. It is, therefore, an extracorporeal blood component collection process.

The instrument utilizes a centrifuge to separate blood components. A disposable apheresis component is connected to the instrument for collection of the desired blood component. The instrument has pumps, clamps, and valves that move and direct donor blood through the component. Part of the component includes a bag into which the desired blood component is collected. Most of the remainder of the component is disposable after completion of the collection process. Such components are often referred to as "disposables".

SUMMARY OF THE INVENTION

Certain examples provide systems, methods, computer program products, and apparatus to authorize a procedure on a biological fluid processing instrument using a disposable component.

Certain examples provide a method for authorizing a procedure using a disposable component. The method includes receiving a disposable component in a biological fluid processing instrument; acknowledging communication between a controller computer and a validation computer in the biological fluid processing instrument; accepting user input of an authentication key via an interface on the validation computer; verifying the authentication key using the validation computer; and disabling the biological fluid processing instrument upon a failure verifying the authentication key.

Certain examples provide a biological fluid processing instrument disposable component authentication system. The system includes a computer facilitating configuration and operation of the biological fluid processing instrument using a disposable component. A first interface is provided by the computer and is used by a service technician to configure the biological fluid processing instrument for a number of disposable components and to provide a service technician with a validation code. A key generator is to accept the validation code from the service technician and generate an authentication key in response to the entered validation code. A second interface is provided by the computer, the second interface prompting the service technician to enter an authentication key, wherein the authentication key authorizes use of a certain number of disposable components for the biological fluid processing instrument.

Certain examples provide a computer readable medium having set of instructions for execution on a computing device. The set of instructions, when executed, configure the computing device to implement a method for authorizing use of a disposable component with a biological fluid processing instrument. The method includes receiving a disposable component in a biological fluid processing instrument; acknowledging communication between a controller computer and a validation computer in the biological fluid processing instrument; accepting user input of an authentication key via an interface on the validation computer; verifying the authentication key using the validation computer; and disabling the biological fluid processing instrument upon a failure verifying the authentication key.

BRIEF DESCRIPTION OF THE DRAWINGS

Certain example embodiments of the invention, together with features and the advantages thereof, may best be understood by reference to the following description taken in conjunction with the accompanying drawings, in which like reference numerals identify like elements in the figures, and in which.

Figure 1:
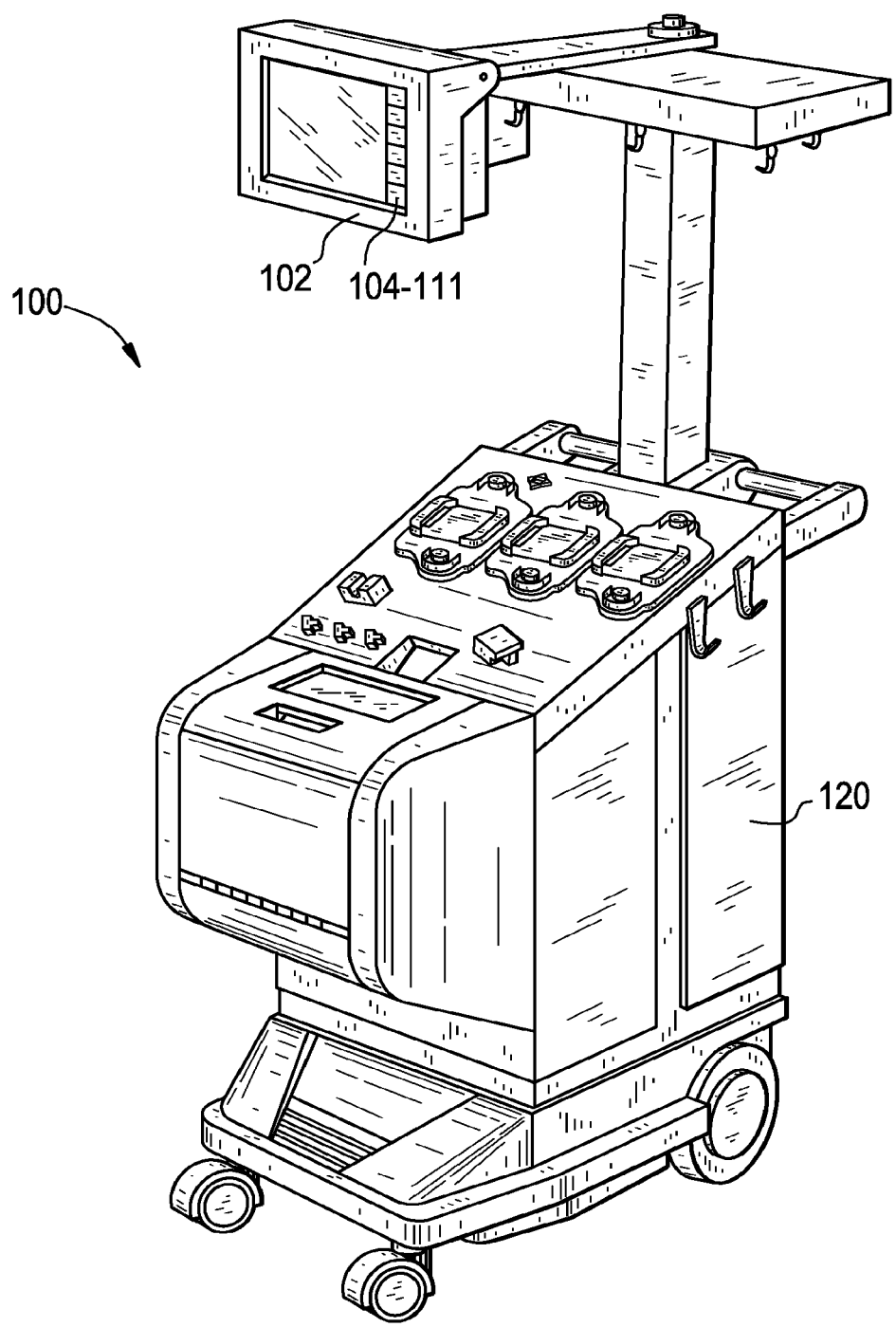
FIG. 1 is a perspective view of a blood processing system with an internal product options calculator.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DESCRIPTION OF CERTAIN EXAMPLES

It will be understood that the present invention may be embodied in other specific forms without departing from the spirit thereof. The present examples and embodiments, therefore, are to be considered in all respects as illustrative and not restrictive, and the invention is not to be limited to the details presented herein.

Although the following discloses example methods, apparatus, systems, and articles of manufacture including, among other components, firmware and/or software executed on hardware, it should be noted that such methods, apparatus, systems and articles of manufacture are merely illustrative and should not be considered as limiting. For example, it is contemplated that any or all of these firmware, hardware, and/or software components could be embodied exclusively in hardware, exclusively in software, exclusively in firmware, or in any combination of hardware, software, and/or firmware. Accordingly, while the following describes example methods, apparatus, systems, and/or articles of manufacture, the examples provided are not the only way(s) to implement such methods, apparatus, systems, and/or articles of manufacture.

In certain examples, use of unauthorized disposables on a biological fluid processing instrument is minimized through user authentication. In addition, user authorization allows for the tracking of the actual number of disposables used. A biological fluid processing instrument can include a blood processing or apheresis system, such as the AMICUS® system, the ALYX® system, etc., to collect one or more blood products from a donor/patient.

FIG. 1 illustrates a blood processing system 100, such as the AMICUS® system commercially available from Fenwal, Inc., for the collection of a blood product. System 100 includes a validation 102 and an internal product options calculator 120. For example, product options calculator 120 can include a digital processor, such as a microprocessor, microcontroller, or the like. The instrument 100 utilizes a centrifuge to separate blood components. A disposable apheresis component is connected to the medical device instrument 100 for collection of the desired blood component. The instrument 100 includes pumps, clamps, and valves that move and direct donor blood through the component. Part of the component includes a bag into which the desired blood component is collected. Most of the remainder of the component is disposable after completion of the collection process. Such components are often referred to as "disposables".

Display 102 can include touch sensitive fields 104-111 for entering default information for the selection of blood component collection information, for example. The settings entered by the touch sensitive fields 104-111 can also be designated as "preselects". These preselects can establish information to be used by the product options calculator in the event that specific information about the donor is not entered prior to a collection procedure. Alternatively and/or in addition, instrument 100 can include one or more input devices for entering default information, such as a keyboard, one or more switches (not shown), one or more buttons (not shown), and/or the like. In certain examples, a set of default parameters can be set up by a user, such as an operator or administrator. Default parameters can be established for single needle procedures, double needle procedures, and/or common defaults for both single and double needle procedures, for example. In certain examples, no information is stored or kept from procedure to procedure for use in a subsequent procedure. However, the presets previously entered by the blood collection center may remain the same for subsequent procedures.

Certain examples can be used in conjunction with one or more blood collection and/or processing devices and can be incorporated into a network of data communication and information exchange between a blood center, blood component collection instruments, and the like. For example, certain examples provide systems, apparatus, and/or methods for collecting, using, and storing information in a biological fluid collection and/or processing facility. Certain examples can be incorporated into an existing facility's system via an upgrade to existing hardware and software. Certain examples provide a data connection between laboratory instruments, including, but not limited to, existing blood and blood component collection instruments, such as the Autopheresis-C, ALYX, and/or AMICUS instruments which are supplied by Fenwal, Inc., such as those systems described in PCT Publication No. WO 01/17584, U.S. Pat. Nos. 5,581,687 and 5,956,023, and U.S. Ser. No. 09/037,356, and biological treatment instruments, such as the pathogen inactivation instruments described in U.S. Ser. No. 09/325,599, which are incorporated by reference herein, and the collection facility's management information system which lends itself to automated tracing and/or tracking of donors and biological fluids data logging. Traceability can be provided via integration of donor, operator, soft goods, and instrument data. In certain examples, event reporting can be automated for regulatory compliance.

In certain examples, the system is designed for a biological fluid collection and/or processing facility as an accessory to the instruments used in those facilities. The general purpose of the system is to increase the efficiency of processing biological fluids and aid in the regulatory compliance process. This purpose is fulfilled principally through the collection of more information and more accurate information. Currently, facility staff must manually keep track of information such as by writing information on a clipboard, but the present system allows the staff and operators to skip the paper/manual steps. The system may also provide some of the following benefits: more accuracy and completeness in the data that is already being collected manually; more data collected for diagnostic use, which may give rise to better information with which to design or troubleshoot laboratory instruments; more data collected for use by the center for generation of ad-hoc statistical reports, which could relate any number of variables such as donors per day/per time of day, rate of errors, collection amount by type of donor, etc.; more data collected for use by the center to determine the efficiency and error rate of different operators, which in turn can inform decisions to institute better training or could substantiate a complaint against a facility operator; greater efficiency on the floor, due to less paperwork; lower costs due to less office paperwork; ability to research all the detailed information on a single procedure, or on the history of a single donor, as a way to find information pertaining to a donor complaint, or something wrong with the product, or any other complaint or error; more complete records and statistical and trend reports to help ease compliance reviews; accurate monitoring of the facility procedures; collection of information that may help the facility's staff improve their efficiency/workflow.

In certain examples, one or more biological fluid processing instruments, laboratory equipment, and/or data input devices are connected to an Ethernet and/or other network along with other data processing applications. Certain examples are also suited for connecting legacy instruments that automatically transmit or can be configured to periodically transmit data via a serial or parallel interface and protocol converters. A computer acting as a server/gateway runs applications to receive the transmitted data and route them to database and hypertext markup language (HTML) applications. Each data packet bears a unique identifier which identifies the source of the data.

In certain examples, users can perform data query and reporting on a local area network, through a wide area network, over the Internet, or a combination of two or more of these, using a standard browser application interface. Real-time viewing and updating of device operation can be configured for any number of devices on the browser. In addition, the server also presents abbreviated data to a wireless personal digital assistant (PDA) also running a standard application browser interface for portable information and viewing and alarm and event notification. The PDAs are also used for data input (through a keypad touch screen, scanning, or other entering method—all used interchangeably herein) in association with an apparatus operation. Thus, certain examples include an open standard architecture in a heterogeneous apparatus environment with real-time update and access of data, and portable data viewing, reporting, notification, and inputting.

Biological fluid processing instrument and/or disposable component usage, authorization, and auditing can be facilitated and monitored via the network and architecture. For example, a validation code including embedded disposable kit usage can be conveyed via a network to a PDA, mobile phone (e.g., smart phone), and/or other computing device. A secondary or tertiary network server can provide validation and/or authorization code(s) to a technician, sales person, and/or other user for disposable kit usage authorization on site, for example. For example, authorization software can reside on a handheld device (e.g., a smartphone) to enable a sales person to approach an apheresis machine and authorize usage of a certain number of disposable kits.

Figure 2:
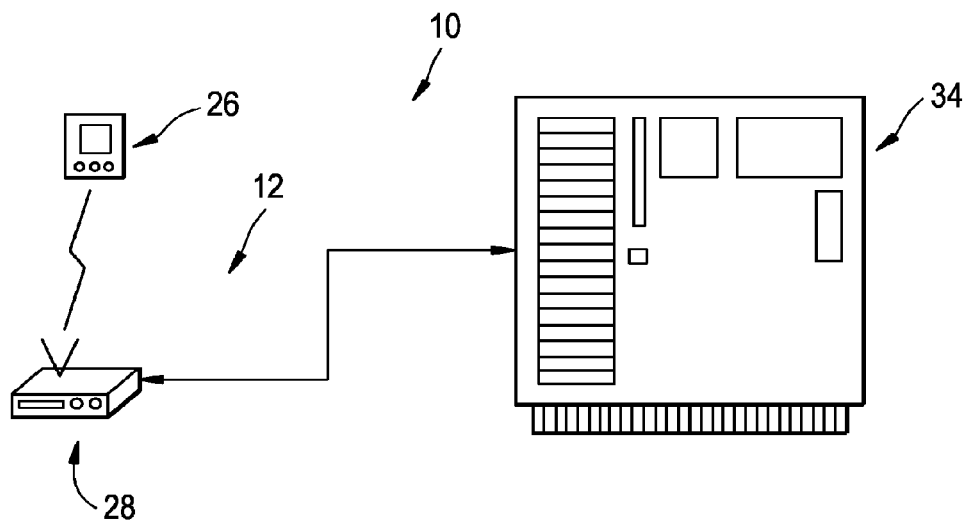
FIGS. 2 through 5 provide example networked systems that can be used in conjunction with the blood collection and/or processing systems described herein.

In certain examples, a biological fluid processing instrument and/or associated authorization/verification system can be included in and/or operate in conjunction with a data communication network. Referring to FIG. 2, for example, the system/apparatus 10 includes a first network 12 comprising a system server 34 including a memory, a communication driver and an HTML application capable of running embedded java script code and at least one wireless data interface, such as a PDA and/or scanner 26. In certain examples, the at least one wireless data interface includes enough PDAs and scanners to accommodate several facility operators and/or donors at a time and a wireless access point 28.

Figure 3:
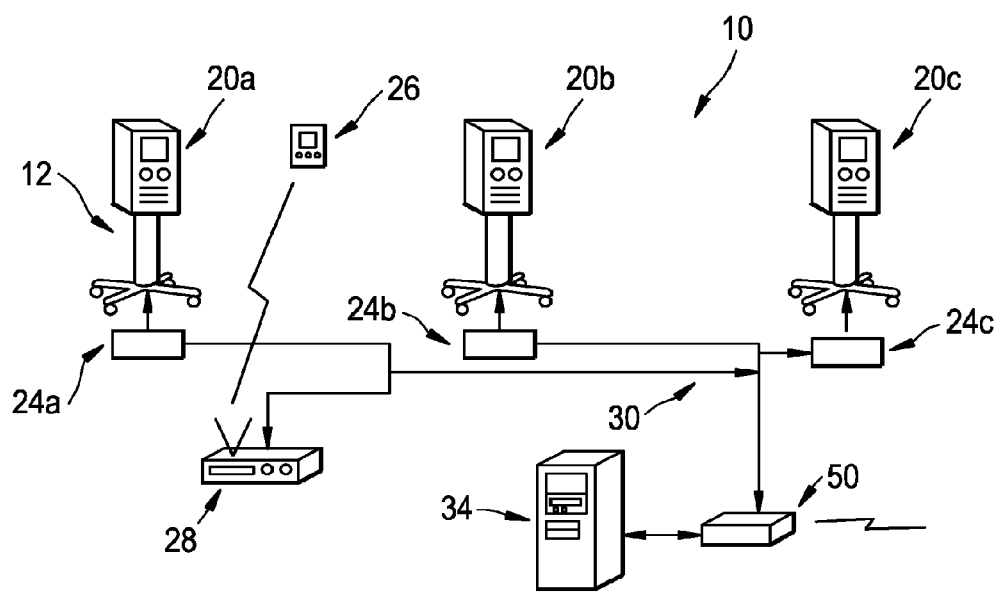

In a second network embodiment illustrated in FIG. 3, the apparatus 10 includes hardware and software component parts and provides for inter-process communication. FIG. 3 shows a first network 12. The first network 12 includes laboratory instruments 20a, 20b, 20c, serial/parallel to Ethernet converters 24a, 24b, 24c, such as a PicoWeb™ device by Lightner Engineering located in San Diego, Calif. or a NetDev™ device by Fenwal Inc., where needed, a first Ethernet 30, and a system server 34 including a memory, a communication driver for the apheresis instruments, a communication protocol converter, and an HTML application with embedded javascript code. The first network 12 can communicate via the Internet through a network switch 50. The network switch 50, which can be incorporated within the system server 34, includes a processor which allows the switch to distinguish the sources of the information which it receives.

Figure 4:
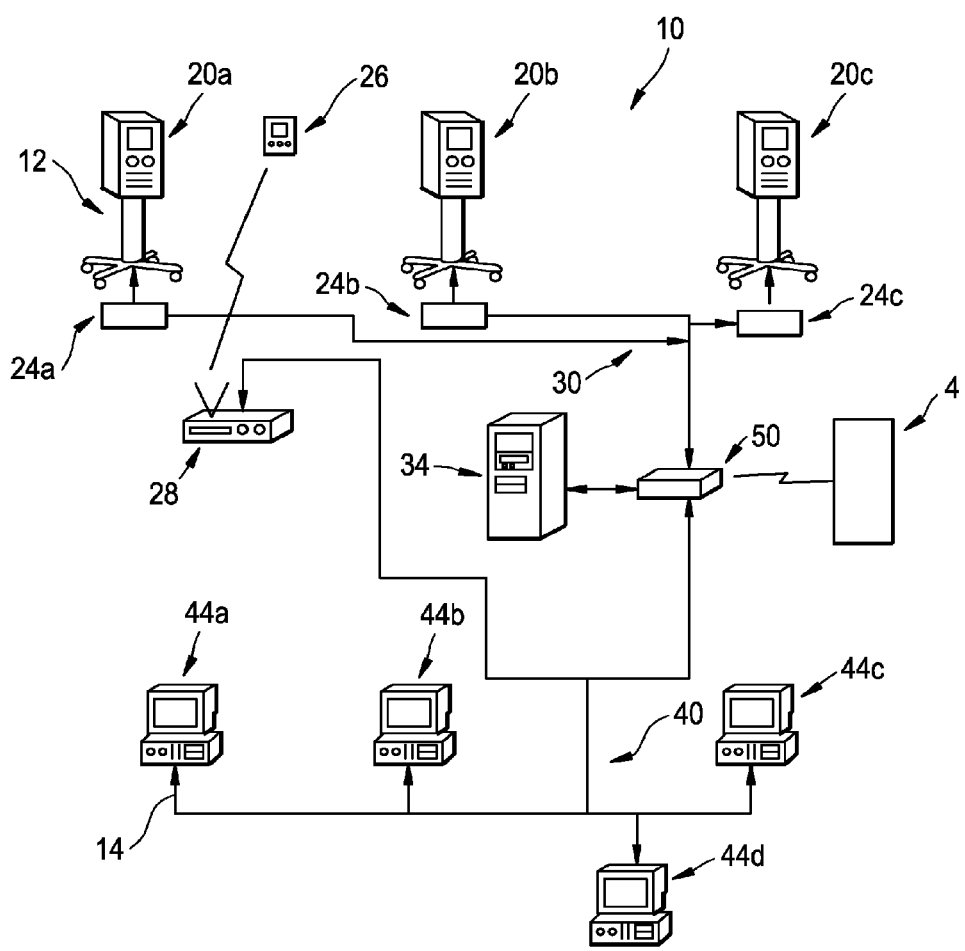

FIG. 4 shows a pair of networks 12, 14. The network switch 50 provides the communication link between the networks 12, 14. Again, the network switch 50 includes a processor which allows the switch to distinguish the sources of the information which it receives. The first network 12 includes laboratory instruments 20a, 20b, 20c, serial/parallel to Ethernet converters 24a, 24b, 24c where needed, a first Ethernet 30, and a system server 34 including a memory, a communication driver for the instruments, a communication protocol converter, and an HTML application capable of running embedded javascript code.

The second network 14 includes a second Ethernet 40 and data interfaces 44a, 44b, 44c, 44d, e.g. personal computers to run server and browser software. At least one of the data interfaces 44a, 44b, 44c is equipped with a barcode scanner for setting up facility operators and associating them with preprinted badges. The second network 14 also includes at least one wireless data interface, preferably a PDA and/or scanner 26, but more preferably enough PDAs and scanners to accommodate several facility operators and/or donors at a time and a wireless access point 28.

A central server 48, generally located at a remote site, may communicate with the first and second networks 12, 14 via the Internet using a communication link such as a modem, digital subscriber line, or the like with the network switch 50. The central server 48, therefore, can access data regarding the instruments 20a, 20b, 20c that are stored in the system server 34.

The first network 12 is primarily established between the system server 34 and the instruments 20a, 20b, 20c. This first network 12 is not directly connected to the Internet or any other subnetwork except through the network switch 50. The network switch 50 is adapted to prevent unwanted communication with external servers and/or other means of data communication while at the same time being configured to forward useable Ethernet datagrams broadcast packets ("UDP") to all ports.

The system server 34 controls the distribution of data, including verification, authorization, and/or auditing data, throughout the system 10. The system server 34 runs an operating system, such as a Linux machine running SuSE 6.4 or more preferably a personal computer running Microsoft 2000. The system server 34 receives data from an instrument 20a via one of the serial/parallel to Ethernet converters 24a and/or other interfaces within the apparatus 10. Accordingly, the system server 34 includes one or more Ethernet cards to connect sets of apheresis instruments 20a, 20b, 20c to the system server 34 and at least one additional Ethernet card to connect the system server 34 to the facility's office network which is also connected to the central server 48. The system server 34 also runs a web server, such as Apache or more preferably Microsoft Internet Information Server provided with Microsoft 2000.

Each instrument 20a, 20b, 20c connected to the apparatus 10 is identified by a unique number such as an internet protocol ("IP") address and a serial number. Certain legacy instruments provide framing bytes on data packets coming through a parallel port. The serial/parallel to Ethernet converters 24a, 24b, 24c gather data from the instruments 20a, 20b, 20c and deliver the data into an Ethernet frame buffer. The data is transmitted via the first Ethernet 30 to the system server 34. Server software takes the data and outputs web pages of information. It should be noted that the Ethernet converters 24a, 24b, 24c are necessary for certain legacy devices and may not be needed in every application of the present system 10.

Figure 5:
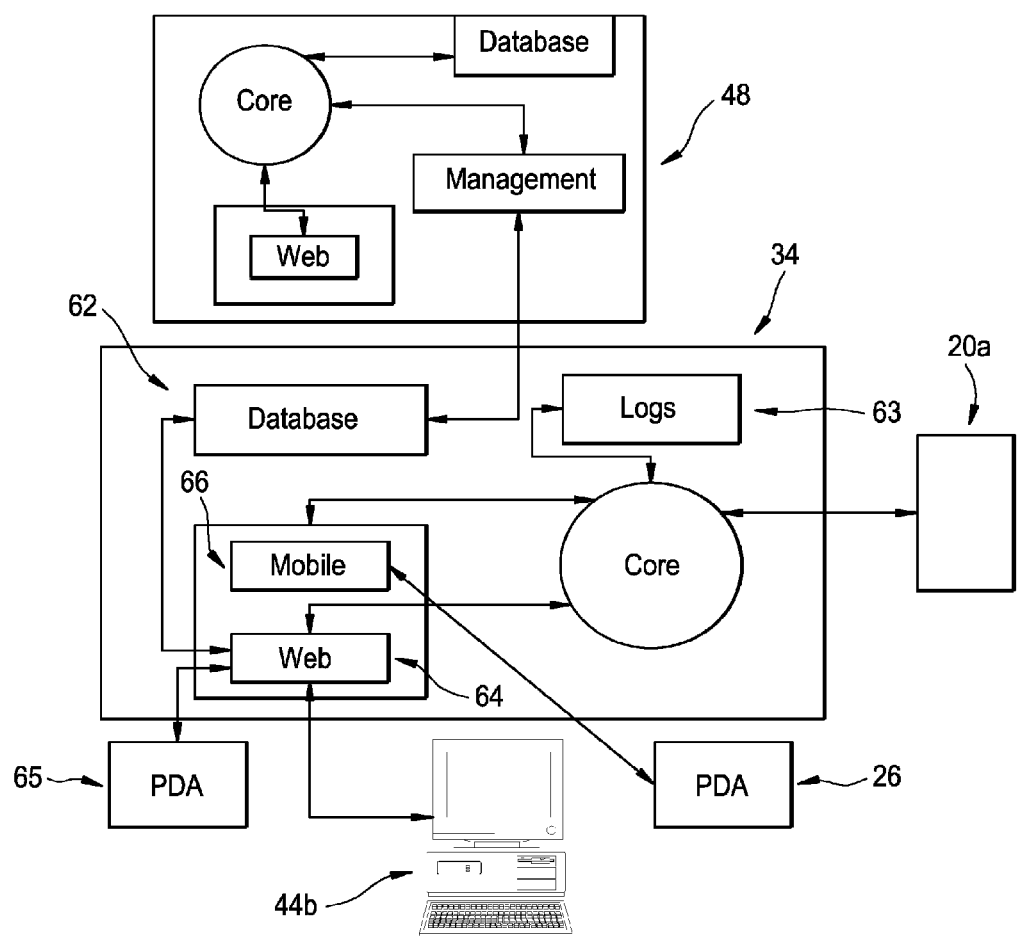

Referring to FIG. 5, the instrument 20a is the primary source of data for the system 10. The instrument 20a may provide parallel data packets to the serial/parallel to Ethernet converter 24a which converts the packets to useable Ethernet datagrams (user datagram protocol/internet protocol ("UDP/IP") packets). The first Ethernet 30 transmits the UDP data packets to the system server 34.

The software within the system server 34 performs two separate functions. The first function gathers data from the instruments 20a, 20b, 20c. This function receives the UDP packets from the first Ethernet 30. The second function outputs HTML files to web clients by sending and receiving remote method invocation ("RMI") data. Accordingly, the server software includes separate modules for performing these functions.

Still referring to FIG. 5, a core module 60, including a java program, communicates with the first Ethernet 30 and also communicates with the other modules within the system server 34. The core module 60 handles access with a database module 62 and caches information from the instrument 20a that is monitored on a frequent basis via data interface 44b and/or the PDAs 26. The core module 60 also writes to a high resolution log filing system 63 and performs the bulk of the business logic. A central or core database 62 (and/or a distributed database implementation) can be used to track disposable kit usage with biological fluid processing machines (e.g., blood processing and/or collection, dialysis, etc.) to facilitate auditing of disposable component usage. Multiple instruments can communicate with the database 62 with usage information (e.g., a number of kits and how often used).

First, the core module 60 receives UDP packets from one of the instruments 20a and tracks the instrument's process. A converter network protocol module includes a protocol describing network communications between the instruments 20a, 20b, 20c and the system server 34 and a converter boot procedure used in conjunction with a bootp server which contains the IP addresses for the instruments 20a, 20b, 20c. The bootp server contains the Internet protocol that enables a diskless workstation to discover its own IP address, the IP address of a bootp server on the network, and a file to be loaded into memory to boot the machine. This enables the workstation to boot without requiring a hard or floppy disk drive. The converter network protocol and the converter boot procedure modules are specifications and not software.

The data transferred from the instruments 20a, 20b, 20c to the core module 60 can be used to create HTML web pages for monitoring the instruments via a structured query language (SQL) open database connectivity interface (ODBC). The core module 60 writes to the database module 62, which includes a SQL database server, to save and manage the instrument data. Javascript is used to create database tables on the SQL server and creates definitions for each table and field. The SQL database server stores all apparatus data except for high resolution logs.

The SQL database server preferably uses MySQL and more preferably Microsoft SQL Server. The SQL database server saves the data into a disk array. Java code within the HTML files provides a SQL interface to the SQL database server 62.

A web module 64, comprising the web server, can access the SQL database server using the ODBC interface. The web module 64 serves the web pages on the second Ethernet 40 so that the instruments 20a, 20b, 20c on the first Ethernet 30 are not interfered. The second Ethernet 40 allows standards such as javascript and hypertext preprocessor (PHP) codes to be viewed. The javascripts and/or PHP can be used to query and search the database.

The web module 64 communicates with the core module 60 via RMI data transmission. The core module 60 sends RMI data to the web module 64. Hypertext transfer protocol (HTTP) data generated by the web module 64 are served to and received from the web browser 44b via the web module 64 and the second Ethernet 40. The web browser 44b can act as a central workstation for monitoring the workflow within the blood collection facility. HTTP data can further be served to and received from the facility's donor management system ("DMS") 65.

A mobile module 66 controls the system server's 34 communications with the PDAs/scanners 26. Thus, PDAs/scanners 26, such as the Palm Pilot™ by Symbol, are also a source of data to the system server 34. Preferably, each PDA/scanner 26 includes a wireless RF link and a built-in bar code scanner. The wireless feature of the PDA/scanner 26 allows the users to move freely in a room such as a blood center and scan barcoded material knowing it was logged into the database. The human error from manually writing down a number onto a log sheet is, thus, eliminated.

The core module 60 communicates with the PDAs/scanners 26 via the mobile module 66 by transmitting and receiving RMI data to and from the mobile module 66. The core module 60 can also serve data regarding the instruments 20a, 20b, 20c, such as an instrument's screen display or status, to a PDA/scanner 26 in real time or near real time. Thus, the wireless access point 28 provides the link between the system server 34 and the PDAs/scanners 26.

The mobile module 66 communicates HTTP data to and from the PDAs/scanners. The PDA/scanner 26 can be used to scan the barcodes of plastic disposable kits, bleed numbers, donor ID cards, operator ID cards, and the instrument itself, and transfer that information to the core module 60 via the mobile module 66. Data that was historically manually recorded at blood centers can now be barcoded and logged electronically and wirelessly via the PDA/scanner 26. Date and time are automatically logged with such information.

Finally, a downtime module contains a java program that performs downtime tasks, including software updates.

The central server 48 is generally located at a remote site and preferably runs a Windows 2000 operating system. The central server 48 is also referred to as a headquarters (HQ) server. The central server 48 is connected to facility networks through an IP network and is, therefore, necessarily more powerful than the facilities' system servers 34 due to the larger database size. The central server 48 must be capable of contacting any remote server at any time. There is not a wireless base station 28 or instrument 20a, 20b, 20c at the HQ level. Personal computers at the headquarters office connect to the central server 48 through HQ office network (IP). Personal computers at the facilities may also connect to the central server 48. Other computer devices with a browser interface and internet/networking capability can also connect to the server with proper security passwords and/or identification.

Similar to the system server 34, the central server 48 includes modules that perform predetermined functions, including a central core module 70, a central database module 70, and a central web module 72. In addition, the central server contains a central management module 74, a database connect file, and an installation procedure.

The central management module 74 is an interactive java program used by HQ management to perform continuous backups and software updates while the database connect file is a file containing the password for the SQL server database. The installation procedure is a procedure for installing server networking and files necessary to start the initial facility network upgrade process, including a setup program.

The central database module 74 houses a database composed of all the facilities' databases merged together. The central database module 74 is designed to facilitate the database merge by insuring that the definitions of unique keys do not conflict. All data is collected by and lives in the facilities' database modules 64. There can be many such facility database modules 64 in communication with the central server 48. The system servers 34 are the servers for all communications with the donor management systems 65.

Optionally, a company operating several facilities, each having its own system server 34, may also have a dedicated central database. This dedicated central database is equivalent to the database module 64 except: (1) many of the functions of the database module 64 cannot be used because the central server 48 is not connected to any wireless devices or apheresis instruments; and (2) an additional program is needed to run the dedicated central database with the contents of the several system databases. This synchronization program communicates directly with the system servers and updates any changes from the system server 34 to the central server 48.

In use, the facilities provide inputs to the system server 34 through an HTTP call for each procedure which is initiated from their donor management system before the system server will store data for the procedure. The facilities may issue HTTP requests for data from their system servers 34 for limited bleed summary fields, using a programmatic interface, in addition to the HTTP browser-based reporting interface from the central server 48.

The apparatus 10 may be called a "distributed system;" however, the system server 34 operates independently as if it were not part of a distributed system. The central or HQ server 48 takes initiative to copy data in both directions as needed.

The system server 34 always operates in server-mode with respect to communications with headquarters and other systems, and never operates in client-mode. The donor management system and the central server 48 operate in client-mode. In server mode, the system server 34 waits for requests and does not initiate transactions with other servers. This achieves the benefits of centralizing data management functions (like backups) while retaining the robustness of independent servers.

Thus, a variety of system, database, and/or network configurations can be used to support validation and authorization of disposable component usage on a fixed, mobile, and/or handheld computing device. Auditing and tracking of disposable component usage can be facilitated on-site and/or remotely using a variety of system, database, and/or network configurations, such as those described above. Multiple instruments at one or more sites can be coordinated and data monitored using such a network system.

In certain examples, one or more authentication schemes can be applied to a biological fluid instrument, such as a blood component collection and/or processing device. An authentication scheme can be used to reduce or help minimize use of unauthorized instrument disposables on a medical device instrument, such as a blood component collection instrument. Using the authentication scheme in conjunction with locking or unlocking device operation can help reduce or minimize the use of unauthorized instrument disposables on a medical device instrument, for example. In addition, the authorization process allows for the tracking of the actual number of disposables used.

Certain examples provide a two step authorization scheme. Each medical device provides a unique validation code (e.g., via an encryption algorithm). The validation code is then used in combination with a number of biological fluid processing disposables to generate an authorization code (e.g. via an encryption algorithm). In some examples, one or more additional parameters, such as site location, customer number, etc., can also be used to generate the authorization code. The authorization code is then input into the biological fluid processing instrument, which would then allow for the use of a certain number of biological fluid processing disposables. Once the number of authorized disposables reaches zero, the biological fluid processing instrument is disabled and/or otherwise becomes non-functional until additional disposables are authorized. The validation code can also include information regarding an actual number of disposables used. This information helps facilitate auditing against the number of disposables sold and provides a secondary way to track use of unauthorized disposables.

In some examples, an individual authorization code is associated with each biological fluid processing disposable. The individual authorization code may be in the form of a unique code number, a unique barcode, a smart card, a radio frequency identifier (RFID), etc. In these examples, an operator of the biological fluid processing instrument inputs an authorization code prior to the use of the biological fluid processing disposable. In addition, a manufacturer of the biological fluid processing disposable places an authorization code on each disposable.

In certain examples, a screen allowing password entry is substituted, added, and/or overlaid on a biological fluid processing device display screen (e.g., an Amicus display screen). A computer, such as an Amicus main processor unit (MPU), sends screen commands to the validation computer to generate a screen display. In this example, the screen sent by the Amicus MPU computer is saved and replaced with a passcode entry screen created by the Amicus validation computer. The validation computer can intercept user interactions and accept key entries without altering the Amicus MPU software and can block further use of the instrument (e.g., the apheresis instrument) by no longer accepting key entries.

Figure 6:
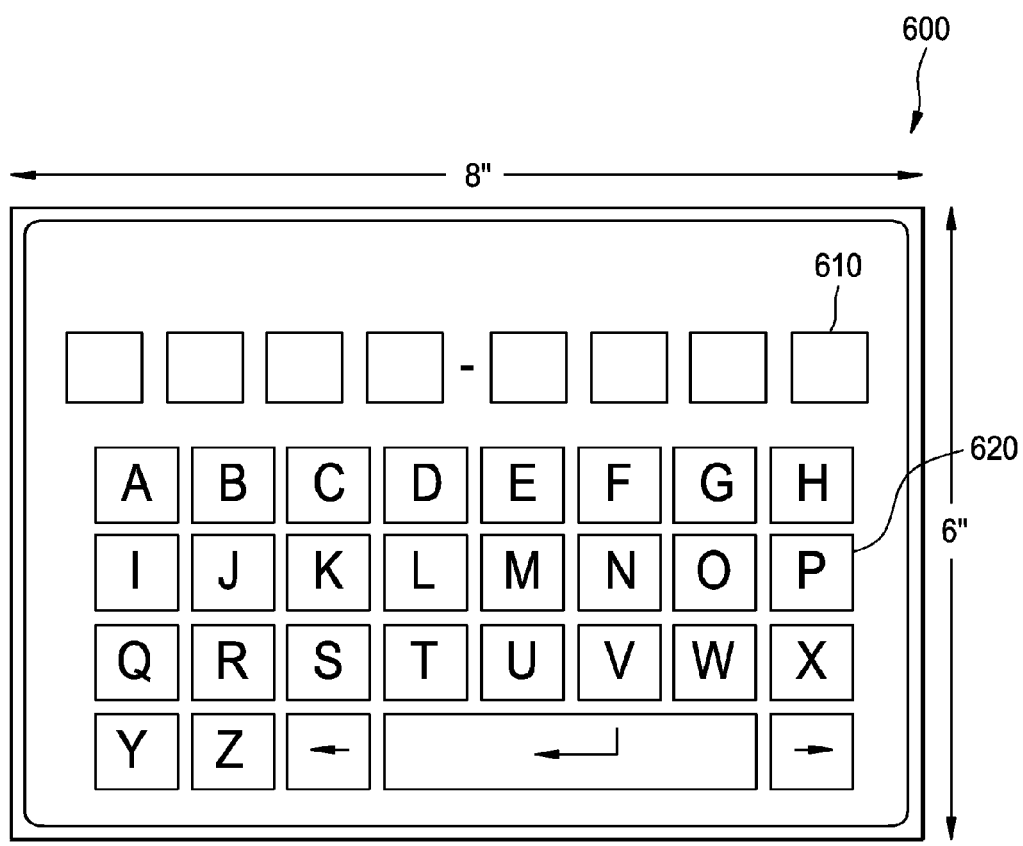
FIG. 6 illustrates an example passcode entry screen.

The passcode entry screen, such as the entry screen 600 shown in FIG. 6, accepts an alphanumeric passcode 810, such as a four digit, eight digit, multiple four-digit combination, etc., passcode. The passcode can be entered via an input 620, such as a keypad, keyboard, touchscreen, etc. In some examples, a card-based (e.g., RFID, magnetic strip, etc.) and/or biometric (e.g., eye-based scan, fingerprint scan, voice-print scan, etc.) can be used for authorization/verification instead of and/or in addition to passcode input verification. If the incorrect passcode is entered, the validation computer does not allow another screen to be displayed. When the correct passcode is entered, the buffered screen sent by the MPU computer is displayed and the instrument continues with normal operation.

In certain examples, the validation computer can stop communicating with the MPU device, which causes the MPU device to go into a safe state and stop operating until the power is cycled. If communication and device operation is halted after priming of the disposable component, the disposable component will be discarded since a primed component cannot be recovered. Therefore, a counterfeit component not matching the authentication code can be destroyed.

Using two computers, one computer controlling a biological fluid processing instrument (e.g., a blood collection and/or processing instrument) and one computer controlling a display with data entry capability, an authentication screen can be displayed that overlays one or more existing screens. The authentication screen can accept a code. If the code is invalid, the validation computer can cease communicating with the computer controlling the instrument, effectively causing the controlling instrument to be unable to advance any given process without the input from the validation computer. If the valid code is entered, the original intended screen can be displayed and the computer controlling the instrument can continue operation as it will now receive appropriate input from the display.

Figure 7:
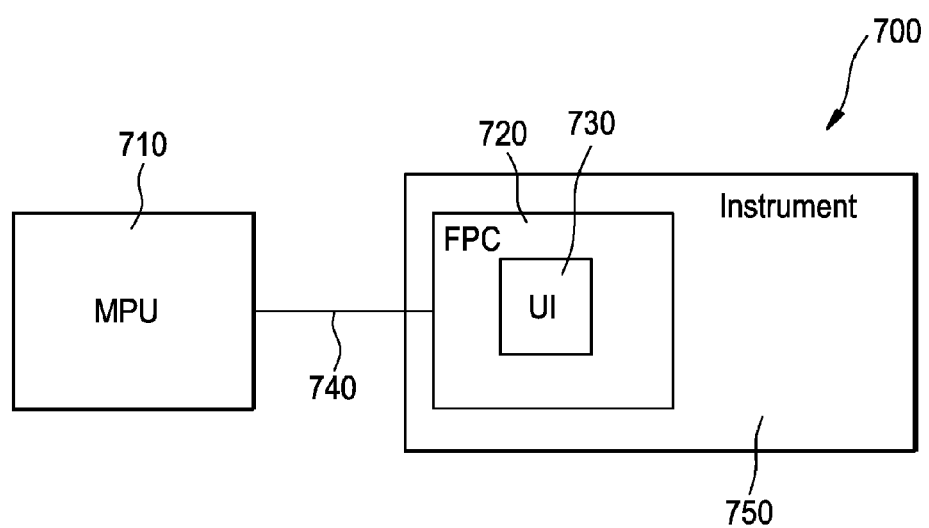
FIG. 7 shows an example of a medical device instrument authentication system.

As shown in FIG. 7, the biological fluid processing instrument authentication system 700 includes two connected computer systems communicating via a communication protocol. The first computer system 710 is the controller. The second computer system 720 is the validation computer. An operator can input and view data on the validation computer via an input 730, such as a touchscreen or keyboard.

The two computers 710, 720 communicate at a regular interval via a communication link 740 (e.g., a wired and/or wireless computer-to-computer, intranet, Internet, and/or other communication link). If at any time the two computers 710, 720 cease to communicate, one or both of computers 710, 720 enter a state in which the operator cannot use them for their normally intended purpose. Since the two computers 710, 720 operate together to meet their intended purpose, the system 700 is inoperable once either computer 710, 720 ceases to function in the expected manner, rendering an associated blood processing instrument 750 temporarily inoperable.

At any time, the computers 710, 720 can request an operator to enter an authentication key. Failure to enter a valid authentication key after a number, X, of attempts can result in the validation computer 720 ceasing to communicate with controller computer. Since normal system 700 operation involves regular communication, the system 700 can cease to function for the intended use.

The system 700 can execute as a part of and/or in conjunction with a biological fluid processing instrument, such as Fenwal's Amicus® device. The Amicus device performs various blood component collection and therapeutic procedures. The Amicus device includes a controller computer known as the Main Processing Unit (MPU) and a validation computer known as the Front Panel Controller (FPC). The Front Panel Controller receives user input via a touchscreen. These two computers send packets of information via a serial protocol. The Main Processing Unit emits a packet of information periodically to the Front Panel Controller. The Front Panel Controller processes the packet and acknowledges by sending a packet back to the Main Processing Unit. If the Main Processing unit fails to send a packet to the Front Panel Controller within X number of seconds, the Front Panel Controller enters a fault mode. If the Front Panel Controller fails to acknowledge a packet from the Main Processor Unit within X number of milliseconds, the Main Processor Unit enters a fault mode.

A disposable component authentication key entry screen is displayed at a point in the procedure. The Front Panel Controller normally draws the screens sent to it as data from the Main Processing Unit. In certain examples, the authentication key entry screen is constructed and controlled in the Front Panel Controller. This allows the Front Panel Controller software to be upgraded independently of the Main Processor Unit. The Front Panel Controller authentication key software can be added to existing software configurations. Since the Front Panel Controller is essentially replacing a screen from the Main Processing Unit temporarily, the intended screen is retained in the validation computer memory until a valid authentication key is received. Once a valid authentication key has been entered, the normal screen is rendered from validation computer memory, and the procedure continues. Failure to enter the authentication key results in the validation computer entering a fault mode which blocks all user input.

In some examples, the timing of when the system enters a fault mode within a procedure is chosen such that an unauthorized component will have been primed. This involves filling the component with fluid in order to displace air. Once a component has been primed, it must be used for the intended procedure. By selecting a location and/or point in time within the procedure such that an unauthorized component will be useless because the procedure has terminated due to authentication failure, the component cannot be recovered.

Certain examples accommodate a variety of ways to accept data entry for an authentication key. Data entry can include a serial connection, a barcode reader, a touchscreen, a keyboard, and/or a data card, for example. Authentication can be used for one or more applications. While the examples provided herein focus on preventing unauthorized disposables from being used on a medical device instrument, any process that makes use of an authentication key can benefit from the dual computer approach. Another example would be password entry to validate authorized users on a computing system (e.g., a blood processing device and/or other computing system).

In some example, an Authentication Code entry screen is included in an apheresis device (e.g., the Amicus QNX) Front Panel Controller (FPC) software. The user receives an authentication code with each disposable component received. After priming the instrument and the component, the validation computer presents a screen to the user requesting the Component Authentication Code. After a certain number of attempts, the validation computer locks and displays a message such as "INVALID COMPONENT, PLEASE USE A GENUINE FENWAL COMPONENT." The operator can then only shutdown the machine, thus making it impossible to use the now primed component and forcing them to throw the component away. Using this approach, the controller computer is not altered, and only the validation computer is modified to provide for the authentication key entry. Changes to authentication and user entry would then involve an update or upgrade to new validation computer but would not necessitate a controller computer update.

In some examples, rather than using a computer application to provide the authorization code, code entry instructions can reside on an authorization server. Service personnel can then login and provide a validation code to generate an authorization code. In some examples, a number of authorized disposables can be automatically generated from other business applications that track sales numbers, a previously used number of disposables (e.g., a three month average), and/or a future forecast of disposables. If the medical device instrument has a direct connect to a network, e.g., a virtual private network and/or the Internet, the authorization server can directly provide an authorization code to the medical device instrument, which would eliminate the need for the service personnel to be at the instrument, for example.

Figure 8:
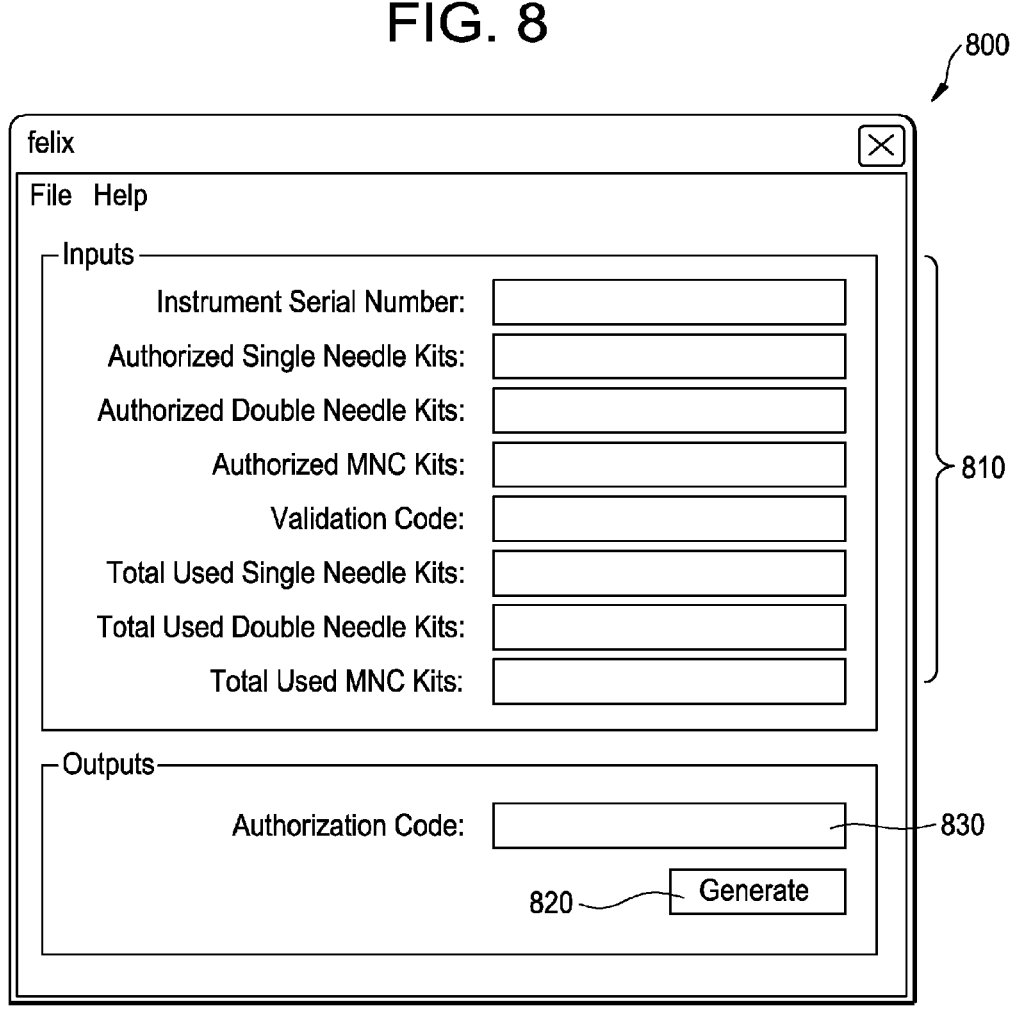
FIG. 8 depicts an example authorization code generation interface.

FIG. 8 depicts an example authorization code generation interface 800. The interface 800 includes a plurality of fields 810 allowing an administrator and/or other operator to provide identifying information such as an instrument serial number, a number of authorized single needle kits, a number of authorized double needle kits, a number of authorized mononuclear cell (MNC) kits, and/or a validation code, etc. Selecting a generate button 820 provides the user with an authorization code 830. The interface 800 can also provide an updated number 840 of used single needle kits, double needle kits, and/or MNC kits, for example, to help a user keep track of available, authorized disposable component inventory and/or to limit a number of components/kits to be used with a single authorization code, for example. Using the interface 800, a user can authorize a certain number of disposable kits and/or other disposable components and can view a number of kits actually used with the instrument. The generated authorization code 830 can include a number of disposable kits used embedded in the code 830 and can facilitate authorized versus counterfeit disposable kit auditing, for example.

Figure 9:
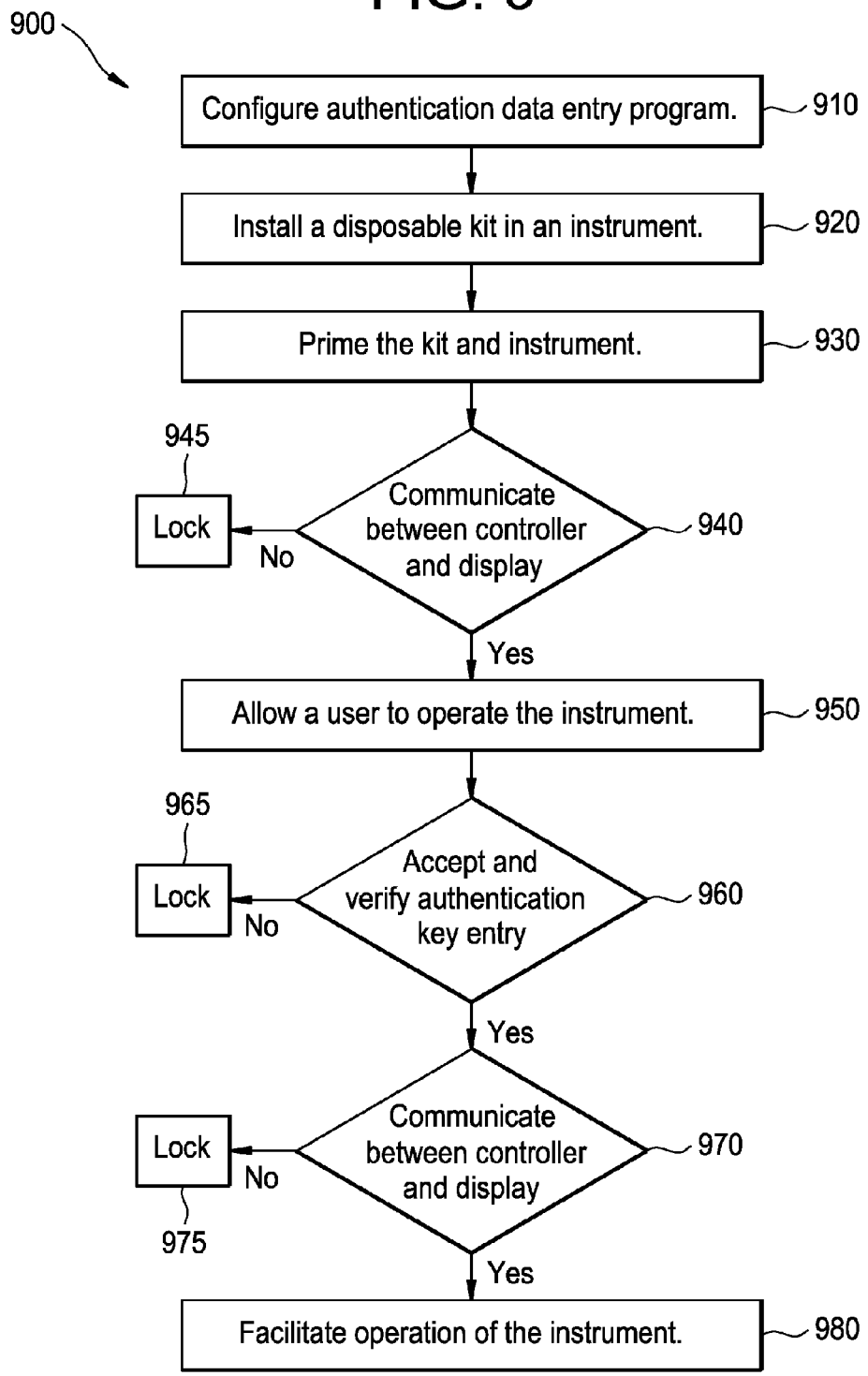
FIG. 9 is a flow chart for a method of user and device authentication with respect to medical device instrument and/or therapeutic procedure execution with a disposable component.

FIG. 9 is a flow chart, generally designated 900, for a method of user and device authentication with respect to biological fluid processing instrument and/or therapeutic procedure execution with a disposable component. At 910, a blood collection and/or processing instrument is configured for operation with respect to a donor/patient. At 920, a disposable component is installed in the instrument. At 930, the instrument is primed with the disposable component. For example, the instrument tests and readies the pressure and fluid flow for blood through the disposable component.

At 940, communication occurs between a controller computer (e.g., an MPU) and a validation computer (e.g., an FPC) in the instrument. Communication occurs to confirm that both the controller computer and the validation computer are operational and connected. Communication between computers can be encrypted, for example. At 945, if communication did not occur between the controller computer and the validation computer, then the instrument is temporarily locked or disabled. That is, if the controller computer and the validation computer are unable to communicate with each other, then the instrument is rendered temporarily inoperable to protect from unauthorized use or malfunction. An authorized operator can check and reinitiate operation of the instrument, for example.

At 950, the instrument operates according to a loaded disposable component and procedure configuration. For example, the instrument initiates operation of a platelet and/or other blood collection procedure for a donor. At 960, the user is prompted for entry of an authentication key. For example, a touchscreen and/or other input on the instrument allows the user to enter an alphanumeric code to authorize use of the instrument and/or the disposable component for a particular procedure. At 965, if a valid authorization code is not entered, then the instrument is temporarily locked and/or disabled. The instrument is locked and/or disabled to prevent unauthorized or fraudulent use of the instrument and/or counterfeit disposable components, for example.

At 970, communication occurs between the controller computer and the validation computer to confirm operation and connectivity of both systems. At 975, if communication did not occur between the controller computer and the validation computer, then the instrument is temporarily locked or disabled. That is, if the controller computer and the validation computer are unable to communicate with each other, then the instrument is rendered temporarily inoperable to protect from unauthorized use or malfunction. An authorized operator can check and reinitiate operation of the instrument, for example.

At 980, operation of the instrument proceeds as configured. For example, if a correct authorization code is entered and the controller computer and validation computer are operational and communicating, then the user can operate the instrument to perform the desired procedure. For example, a whole blood and/or blood component collection procedure is launched to collect whole blood or one or more blood components from a donor. In another example, a blood processing and filtration procedure is launched to treat a patient (such as a patient with a kidney condition.

The blocks of the method 900 can be implemented in the order shown in FIG. 9 and/or in one or more variations of that order. In certain examples, one or more blocks can be skipped or omitted. The blocks of the method 900 can be implemented in one or more combinations of hardware, software, and/or firmware, for example. For example, the blocks of the method 900 can be implemented as a set of instructions for execution on a computer and/or other machine readable medium, such as a disk, hard drive, and/or other memory (RAM, ROM, Flash, etc.).

Figure 10:
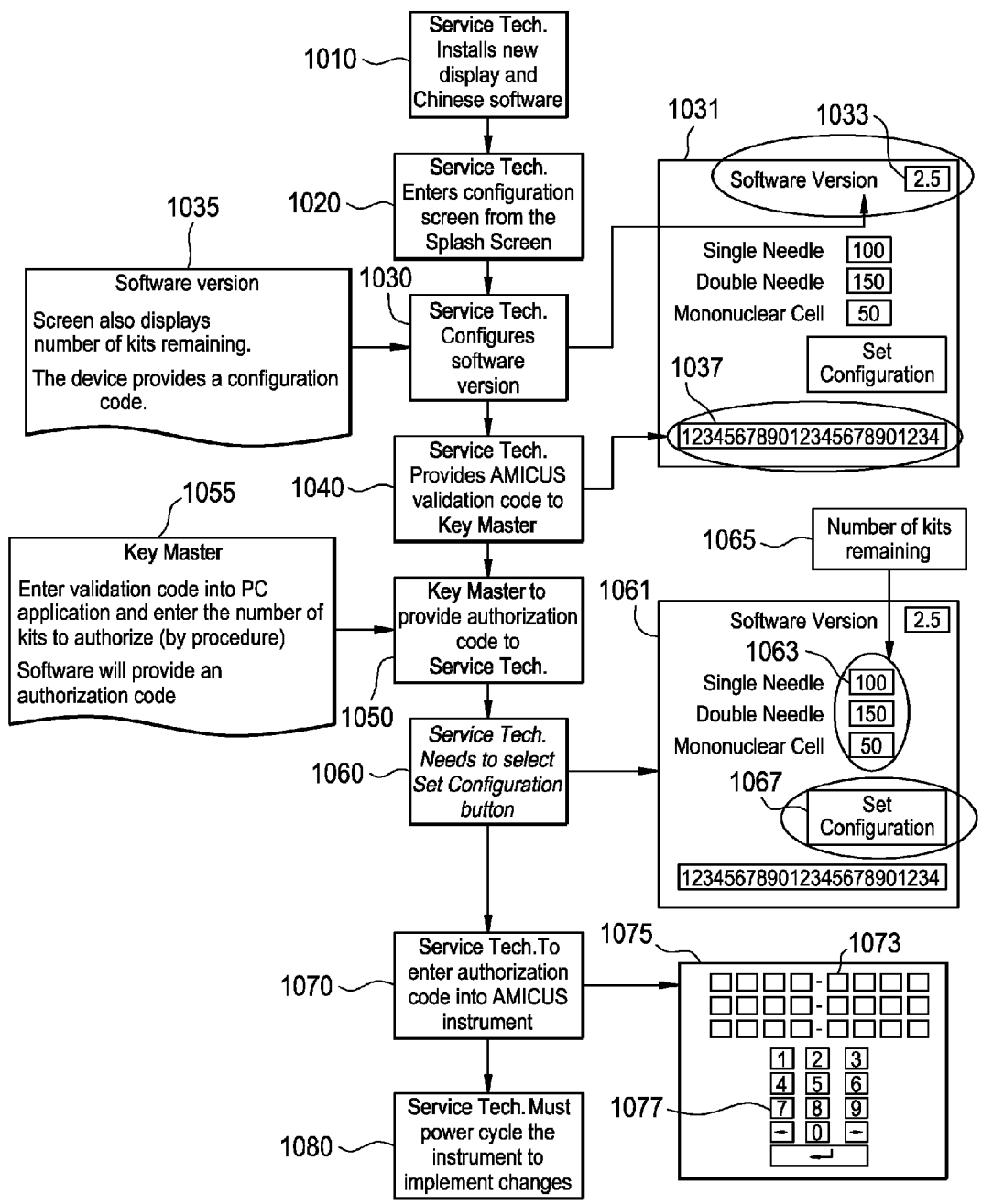
FIG. 10 illustrates a system and process flow diagram to configure and authorize use of a medical device instrument.

FIG. 10 illustrates a system and process flow diagram, generally labeled 1000, to configure and authorize use of a biological fluid processing instrument. At 1010, a service technician installs a validation computer on a biological fluid processing instrument (e.g., an apheresis device). At 120, the service technician enters a configuration screen to configure the instrument. At 1030, the service technician configures the version of the validation computer being installed on the instrument. A screen 1031 provides software version information 1033, a number of disposable kits remaining 1036, and a configuration code 1037 for use by the technician 1039 in configuring the instrument. The configuration code 1037 can include an indication of a number of disposable kits used by the instrument, for example.

At 1040, the service technician provides the instrument validation or configuration code to a key master 1055. At 1050, the key master 1055 provides an authorization code to the service technician. At 1060, the service technician sets the configuration via an interface screen 1061. A number of kits remaining 1065 is provided for single needle, double needle, and MNC procedures. A user can set the instrument configuration 1067 via the interface 1061 based on the provided information.

At 1070, the service technician enters the authorization code into one or more fields 1073 of an interface screen 1075 provided on the biological fluid processing instrument via a touchscreen and/or other keypad 1077. At 1080, the service technician cycles power to the instrument to implement changes. In some examples, once the number of components remaining reaches zero, a loss of communication message is displayed after a procedure is selected. A user will not be able to proceed until additional authorized components are provided for the procedure. A number of components remaining 1065 is also provided.

Thus, the service technician can pull up an interface screen to retrieve a configuration code specific to the instrument. The technician can provide the configuration code to generate an authorization code based on system knowledge of how many disposable kits to be authorized for a given instrument. The generated authorization code can be provided to the instrument to authorize a certain number of disposable components for use with the instrument.

The blocks of FIG. 10 can be implemented in the order shown in FIG. 10 and/or in one or more variations of that order. In certain examples, one or more blocks can be skipped or omitted. The blocks of FIG. 10 can be implemented in one or more combinations of hardware, software, and/or firmware, for example. For example, the blocks of FIG. 10 can be implemented as a set of instructions for execution on a computer and/or other machine readable medium, such as a disk, hard drive, and/or other memory (RAM, ROM, Flash, etc.).

Figure 11:
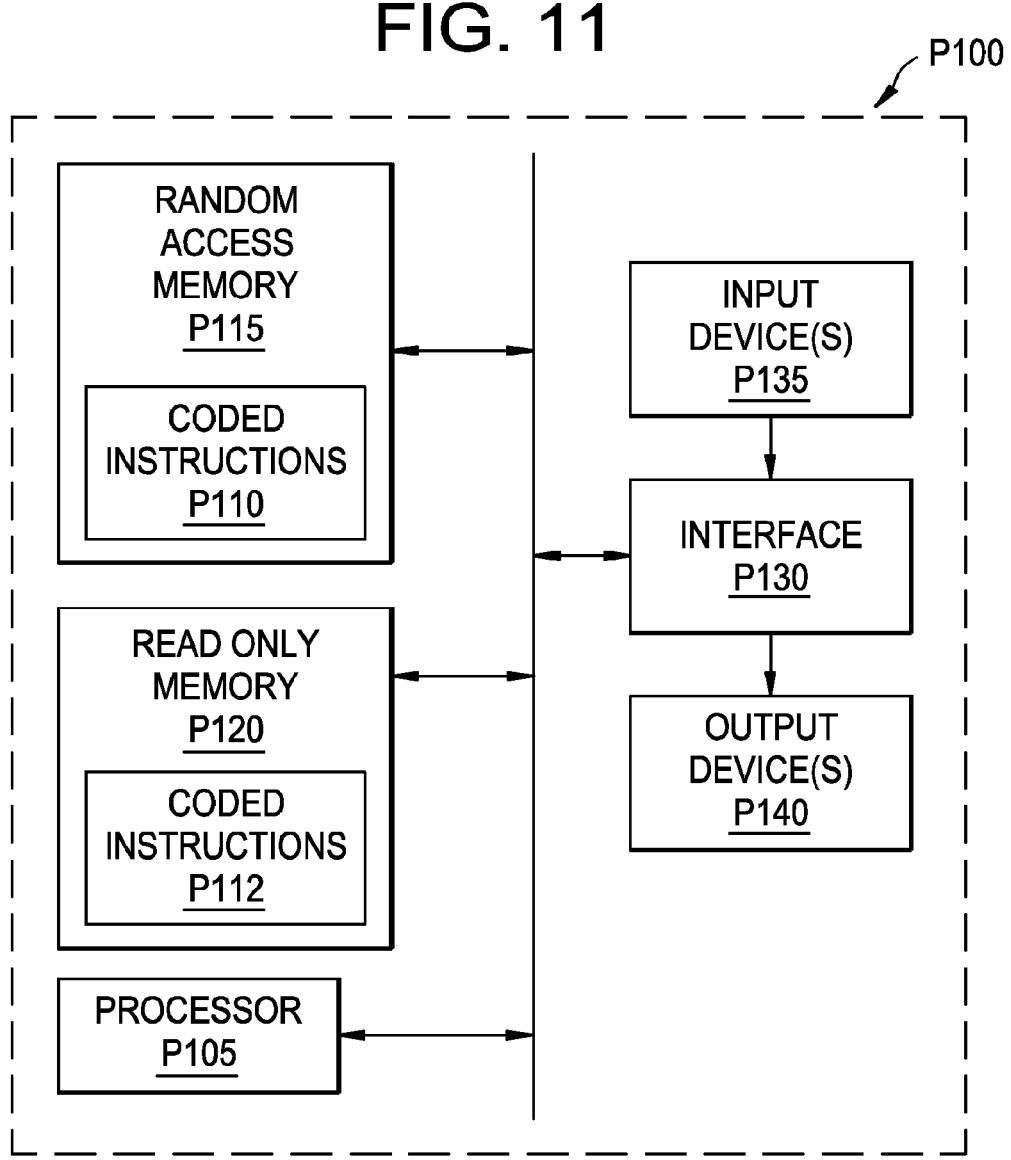
FIG. 11 is a schematic diagram of an example processor platform that can be used and/or programmed to implement the example systems and methods described herein.

FIG. 11 is a schematic diagram of an example processor platform P100 that can be used and/or programmed to implement the example systems and methods described above. For example, the processor platform P100 can be implemented by one or more general-purpose processors, processor cores, microcontrollers, etc.

The processor platform P100 of the example of FIG. 11 includes at least one general-purpose programmable processor P105. The processor P105 executes coded instructions P110 and/or P112 present in main memory of the processor P105 (e.g., within a RAM P115 and/or a ROM P120). The processor P105 may be any type of processing unit, such as a processor core, a processor and/or a microcontroller. The processor P105 may execute, among other things, the example processes of FIGS. 9-10 to implement the example methods and apparatus described herein.

The processor P105 is in communication with the main memory (including a ROM P120 and/or the RAM P115) via a bus P125. The RAM P115 may be implemented by dynamic random access memory (DRAM), synchronous dynamic random access memory (SDRAM), and/or any other type of RAM device, and ROM may be implemented by flash memory and/or any other desired type of memory device. Access to the memory P115 and the memory P120 may be controlled by a memory controller (not shown). The example memory P115 may be used to implement the example databases described herein.

The processor platform P100 also includes an interface circuit P130. The interface circuit P130 may be implemented by any type of interface standard, such as an external memory interface, serial port, general-purpose input/output, etc. One or more input devices P135 and one or more output devices P140 are connected to the interface circuit P130. The input devices P135 may be used to, for example, receive patient documents from a remote server and/or database. The example output devices P140 may be used to, for example, provide patient documents for review and/or storage at a remote server and/or database.

Thus, certain examples provide authorization for use of disposables in a blood collection and/or processing instruments. Certain examples generate an authorization code for instrument configuration for a blood collection and/or processing procedure. Certain examples help simplify and avoid errors in procedure selection and instrument configuration for collection and/or processing of one or more blood components (e.g., whole blood, platelets, red blood cells, and/or plasma) to be collected from a donor.

While particular embodiments of the invention have been shown and described, it will be obvious to those skilled in the art that changes and modifications may be made therein without departing from the invention in its broader aspects.

It will be appreciated by persons skilled in the art that numerous variations and/or modifications may be made to the invention as shown in the specific embodiments and/or aspects without departing from the spirit or scope of the invention as broadly described. The present embodiments and aspects are, therefore, to be considered in all respects as illustrative and not restrictive. Several embodiments are described above with reference to the drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems and program products on any electronic device and/or machine-readable media suitable for accomplishing its operations. Certain embodiments of the present invention may be implemented using an existing computer processor and/or by a special purpose computer processor incorporated for this or another purpose or by a hardwired system, for example.

Embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

The invention claimed is:

1. A method for authorizing use of a medical instrument with a disposable component, the disposable component to be received in the medical instrument, the method comprising:
   accepting input of an authentication key via an interface provided by a computer, the authentication key associated with a number of authorized uses, the authentication key generated from a validation code and a number of disposables for the medical instrument;
   verifying the authentication key using the computer; and
   authorizing use of the medical instrument upon verification of the authentication key.

2. The method of claim 1, wherein the authentication key is provided with the disposable component as a single use authentication key.

3. The method of claim 1, wherein the authentication key is rendered invalid after the number of authorized uses has been exceeded, a count of the number of uses to increment after each authorized use of the biological fluid processing instrument.

4. The method of claim 1, wherein the authentication key is provided via at least one of a data card, a radio frequency identifier, a barcode, a personal digital assistant, a mobile phone and a disk-based medium.

5. The method of claim 1, wherein the interface is an RFID interface and the authentication key is received by the RFID interface.

* * * * *